United States Patent
Lee

(10) Patent No.: US 12,243,224 B2
(45) Date of Patent: Mar. 4, 2025

(54) MEDICAL IMAGE ANALYSIS METHOD, MEDICAL IMAGE ANALYSIS APPARATUS, AND MEDICAL IMAGE ANALYSIS SYSTEM FOR QUANTIFYING JOINT CONDITION

(71) Applicant: CRESCOM CO., LTD., Seongnam-si (KR)

(72) Inventor: Jae Joon Lee, Yongin-si (KR)

(73) Assignee: CRESCOM CO., LTD., Seongnam-si (KR)

(*) Notice: Subject to any disclaimer, the term of this patent is extended or adjusted under 35 U.S.C. 154(b) by 365 days.

(21) Appl. No.: 17/634,761

(22) PCT Filed: Dec. 3, 2021

(86) PCT No.: PCT/KR2021/018218
§ 371 (c)(1),
(2) Date: Feb. 11, 2022

(87) PCT Pub. No.: WO2023/017919
PCT Pub. Date: Feb. 16, 2023

(65) Prior Publication Data
US 2023/0360198 A1    Nov. 9, 2023

(30) Foreign Application Priority Data
Aug. 11, 2021    (KR) ................. 10-2021-0105754

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4528* (2013.01); *G06T 7/11* (2017.01);
(Continued)

(58) Field of Classification Search
CPC ......... G06T 7/0012; G06T 7/11; G06T 7/155; G06T 7/60; G06T 7/73;
(Continued)

(56) References Cited

U.S. PATENT DOCUMENTS

2016/0180520 A1*    6/2016    Huo ................. G06T 7/0012
382/131

FOREIGN PATENT DOCUMENTS

| JP | 2004-57804 A | 2/2004 |
| JP | 2016-144535 A | 8/2016 |

(Continued)

OTHER PUBLICATIONS

Cheung, J.C.W., Tam, A.Y.C., Chan, L.C., Chan, P.K. and Wen, C., 2021. Superiority of multiple-joint space width over minimum-joint space width approach in the machine learning for radiographic severity and knee osteoarthritis progression. Biology, 10(11), p. 1107.*

(Continued)

*Primary Examiner* — Zhitong Chen
(74) *Attorney, Agent, or Firm* — Sughrue Mion, PLLC

(57) ABSTRACT

Provided is a medical image analysis method including acquiring a target medical image, detecting a target joint spacing region from the target medical image, acquiring a first value related to a width of a joint part from the target medical image, acquiring a second value related to joint spacing from the target joint spacing region, and calculating a target joint condition indicator indicating a joint condition based on the first value and the second value.

11 Claims, 13 Drawing Sheets

(51) Int. Cl.
*G06T 7/11* (2017.01)
*G06T 7/155* (2017.01)
*G06T 7/60* (2017.01)
*G06T 7/73* (2017.01)
*G16H 30/40* (2018.01)
*G16H 50/30* (2018.01)

(52) U.S. Cl.
CPC ............... *G06T 7/155* (2017.01); *G06T 7/60* (2013.01); *G06T 7/73* (2017.01); *G16H 30/40* (2018.01); *G16H 50/30* (2018.01); *G06T 2207/20021* (2013.01); *G06T 2207/20036* (2013.01); *G06T 2207/20081* (2013.01); *G06T 2207/20084* (2013.01); *G06T 2207/30008* (2013.01)

(58) Field of Classification Search
CPC . G06T 2207/20021; G06T 2207/20036; G06T 2207/20081; G06T 2207/20084; G06T 2207/30008; G06T 7/136; G06T 7/62; G06T 2210/41; A61B 5/4528; A61B 5/1075; A61B 5/1079; G16H 30/40; G16H 50/30; G16H 30/20; G06N 3/0464; G06N 3/045; G06N 3/08
See application file for complete search history.

(56) References Cited

FOREIGN PATENT DOCUMENTS

| | | |
|---|---|---|
| JP | 2021-23548 A | 2/2021 |
| KR | 10-2016-0103562 A | 9/2016 |
| KR | 10-2018-0092797 A | 8/2018 |
| KR | 10-1968144 B1 | 8/2019 |

OTHER PUBLICATIONS

Japanese Office Action dated Sep. 26, 2023 in Application No. 2022-508473.

* cited by examiner

MEDICAL IMAGE ANALYSIS METHOD, MEDICAL IMAGE ANALYSIS APPARATUS, AND MEDICAL IMAGE ANALYSIS SYSTEM FOR QUANTIFYING JOINT CONDITION

CROSS REFERENCE TO RELATED APPLICATIONS

This application is a National Stage of International Application No. PCT/KR2021/018218 filed Dec. 3, 2021, claiming priority based on Korean Patent Application No. 10-2021-0105754 filed Aug. 11, 2021.

TECHNICAL FIELD

The present disclosure relates to a medical image analysis method, a medical image analysis apparatus, and a medical image analysis system. More particularly, the present disclosure relates to a medical image analysis method, a medical image analysis apparatus, and a medical image analysis system for calculating joint condition information that quantifies a joint condition.

BACKGROUND ART

With improvements in image segmentation technology, the field of medical image analysis capable of calculating diagnostic auxiliary indicators related to various diseases by segmenting medical images has recently been attracting attention. In particular, in order to provide joint condition information, medical image analysis technology is being studied in various fields.

In analyzing joint conditions, one of the most important factors is joint spacing, and a reduction in joint spacing is known to have an important relationship with rheumatoid arthritis, degenerative arthritis, a wear status of cartilage, joint conditions in various parts of the body, and the like. In particular, many studies have demonstrated that a joint spacing value has a significant relationship with joint pain.

Conventionally, however, joint conditions are estimated based on an absolute value of joint spacing. However, the absolute value of joint spacing may vary significantly depending on external factors such as sex, race, and body type. In addition, errors may occur in the absolute value of joint spacing depending on a system and program of an imaging device that captures an image. In this case, even if an error on a millimeter scale occurs, the change in the value is large, and it may lead to inaccurate results in finding a reduction rate of joint spacing compared to normal, comparing with other patients, or monitoring prognosis. In other words, there is a limit to finding a joint condition based on the absolute value of joint spacing. Accordingly, there is a need to develop a medical image analysis method, a medical image analysis apparatus and a medical image analysis system capable of acquiring objective joint condition information by minimizing the influence of external factors.

DISCLOSURE

Technical Problem

The present disclosure is directed to providing a medical image analysis method, a medical image analysis apparatus, and a medical image analysis system for calculating joint condition information.

Objects to be solved by the present disclosure are not limited to the above-described objects, and objects that are not mentioned will be clearly understood by those skilled in the art to which the present disclosure pertains from the present specification and the accompanying drawings.

Technical Solution

One aspect of the present disclosure provides a medical image analysis method including acquiring a target medical image, detecting a target joint spacing region from the target medical image, acquiring a first value related to a width of a joint part from the target medical image, acquiring a second value related to joint spacing from the target joint spacing region, and calculating a target joint condition indicator indicating a joint condition based on the first value and the second value.

Another aspect of the present disclosure provides a medical analysis apparatus including an image acquisition unit configured to acquire a target medical image, and a controller configured to provide joint condition information based on the target medical image, in which the controller acquires a target medical image, detects a target joint spacing region from the target medical image, acquires a first value related to a width of a joint part from the target medical image, acquires a second value related to joint spacing from the target joint spacing region, and calculates a target joint condition indicator indicating the joint condition based on the first value and the second value.

Technical solutions of the present disclosure are not limited to the above-described solutions, and solutions that are not mentioned will be clearly understood by those skilled in the art to which the present disclosure pertains from the present specification and the accompanying drawings.

Advantageous Effects

According to a medical image analysis method, a medical image analysis apparatus, and a medical image analysis system according to an embodiment of the present disclosure, it is possible to acquire objective joint condition information by minimizing the influence of external factors such as body type, race, and sex.

Effects of the present disclosure are not limited to the above-described effects, and effects that are not described will be clearly understood by those skilled in the art to which the present disclosure pertains from the present specification and the accompanying drawings.

BEST MODE

Figure 1:
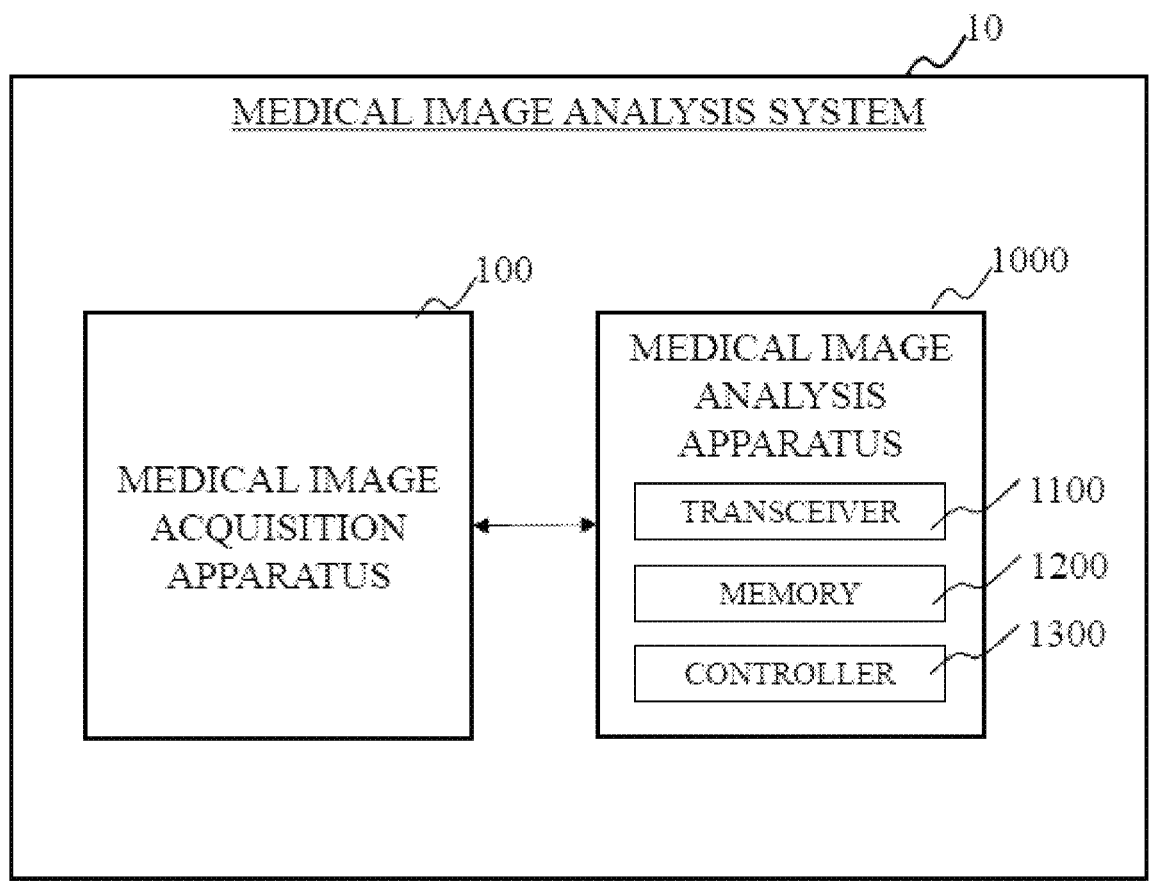
FIG. 1 is a schematic diagram of a medical image analysis system according to an embodiment of the present disclosure.

According to an embodiment of the present disclosure, a medical image analysis method may include: acquiring a target medical image; detecting a target joint spacing region from the target medical image; acquiring a first value related to a width of a joint part from the target medical image; acquiring a second value related to joint spacing from the target joint spacing region; and calculating a target joint condition indicator indicating a joint condition based on the first value and the second value.

According to an embodiment of the present disclosure, the detecting of the target joint spacing region may include: detecting a region of interest (ROI) from the target medical image; and performing segmentation on the ROI to acquire the target joint spacing region included in the ROI.

According to an embodiment of the present disclosure, the ROI may be acquired using a first neural network model trained to receive the medical image and output a region including a joint part.

According to an embodiment of the present disclosure, the segmentation may be performed using a second neural network model trained to receive a medical image including a region of interest (ROI) and output a joint spacing region.

According to an embodiment of the present disclosure, the acquiring of the first value may include: detecting a first point and a second point adjacent to a boundary between a bone region and an outer region of the bone from the target medical image; acquiring first coordinate information of the first point and second coordinate information of the second point; and calculating the first value based on the first coordinate information and the second coordinate information.

According to an embodiment of the present disclosure, the first point and the second point may be acquired based on a difference between brightness of the bone region included in the target medical image and brightness of the outer region of the bone.

According to an embodiment of the present disclosure, the first point and the second point may be acquired through a neural network model trained to receive a medical image including the bone region and the outer region of the bone and output a first region corresponding to the first point and a second region corresponding to the second point.

According to an embodiment of the present disclosure, the acquiring of the second value may include: acquiring a section of interest in the joint spacing region; acquiring a plurality of joint spacing values within the section of interest; and acquiring the second value based on the plurality of joint spacing values.

According to an embodiment of the present disclosure, the second value may be a minimum value among the plurality of joint spacing values or an average value of the plurality of joint spacing values.

According to an embodiment of the present disclosure, the target joint condition indicator may be defined as a ratio of the second value to the first value.

According to an embodiment of the present disclosure, there may be provided a computer-readable recording medium on which a program for executing the medical image analysis method is recorded.

According to an embodiment of the present disclosure, a medical image analysis apparatus for calculating information related to a joint condition by analyzing a medical image may include: an image acquisition unit configured to acquire a target medical image; and a controller configured to provide joint condition information based on the target medical image, in which the controller may acquire the target medical image, detect a target joint spacing region from the target medical image, acquire a first value related to a width of a joint part from the target medical image, acquire a second value related to joint spacing from the target joint spacing region, and calculate a target joint condition indicator indicating the joint condition based on the first value and the second value.

MODES OF THE INVENTION

The above-described objects, features, and advantages of the present disclosure will become more obvious from the following detailed description provided in relation to the accompanying drawings. However, the present disclosure may be variously modified and have several embodiments. Therefore, specific embodiments of the present disclosure will be illustrated in the accompanying drawings and described in detail.

In principle, the same reference numerals denote the same constituent elements throughout the specification. Further, elements having the same function within the scope of the same idea illustrated in the drawings of each embodiment will be described using the same reference numerals, and overlapping descriptions thereof will be omitted.

When it is decided that a detailed description of a known function or configuration related to the present disclosure may obscure the gist of the present disclosure, the detailed description will be omitted. In addition, numbers (for example, first, second, etc.) used in the course of describing the present specification are only identification symbols for distinguishing one component from other components.

In addition, suffixes "module" and "unit" for components used in the following embodiments are used only in order to make the disclosure easy.

Therefore, these terms do not have different meanings or roles from each other in themselves.

In the following embodiments, singular forms include plural forms unless interpreted otherwise in context.

In the following embodiments, the terms "include" or "have" mean that a feature or element described in the specification is present, and do not preclude in advance the possibility that one or more other features or components may be added.

Sizes of components may be exaggerated or reduced in the accompanying drawings for convenience of explanation. For example, the size and thickness of each component illustrated in the drawings are arbitrarily indicated for convenience of description, and the present disclosure is not necessarily limited to those illustrated.

In a case where certain embodiments can be otherwise implemented, the order of specific processes may be performed differently from the order in which the processes are described. For example, two processes described in succession may be performed substantially simultaneously, or may be performed in an order opposite to the order described.

In the following embodiments, when components are connected, it includes not only a case where the components are directly connected but also a case where the components are indirectly connected via a certain component interposed between the components.

For example, in the present specification, when components and the like are electrically connected, it includes not only a case where the components are directly electrically connected, but also a case where the components are indirectly electrically connected via a certain component interposed between the components Hereinafter, a medical image analysis method, a medical image analysis apparatus, and a medical image analysis system of the present disclosure will be described with reference to FIGS. 1 to 13.

FIG. 1 is a schematic diagram of a medical image analysis system 10 according to an embodiment of the present disclosure.

The medical image analysis system 10 according to the embodiment of the present disclosure may include a medical image acquisition apparatus 100 and a medical image analysis apparatus 1000.

The medical image acquisition apparatus 100 may capture a medical image. For example, the medical image acquisition apparatus 100 may be any device for capturing any type of medical images such as magnetic resonance imaging equipment, computerized tomography equipment, X-ray equipment, or the like. The medical image acquired by the medical image acquisition apparatus 100 may be a two-dimensional image. In this case, the medical image may include pixel information related to coordinates, color, intensity, and the like of a pixel. The medical image acquired by the medical image acquisition apparatus 100 may be a three-dimensional image. In this case, the medical image may include pixel information related to coordinates, color, intensity, and the like of a voxel.

The medical image analysis apparatus 1000 according to the embodiment of the present disclosure may acquire joint condition information by analyzing a medical image. More specifically, the medical image analysis apparatus 1000 may detect a joint region from the medical image and quantify information related to a joint condition based on the joint region. Here, the joint region may include an inter-joint region (or joint spacing region), a bone region adjacent to the inter-joint region, and the like.

The medical image analysis apparatus 1000 according to the embodiment of the present disclosure may include a transceiver 1100, a memory 1200, and a controller 1300.

The transceiver 1100 of the medical image analysis apparatus 1000 may communicate with any external device including the medical image acquisition apparatus 100. For example, the medical image analysis apparatus 1000 may receive a medical image captured by the medical image acquisition apparatus 100 through the transceiver 1100. Also, the medical image analysis apparatus 1000 may transmit the acquired joint condition information to any external device including the medical image acquisition apparatus 100 through the transceiver 1100.

The medical image analysis apparatus 1000 may be connected to a network through the transceiver to transmit/receive various types of data. Types of the transceiver may largely include a wired type and a wireless type. Since the wired type and the wireless type have their respective strengths and weaknesses, in some cases, the wired type and the wireless type may be simultaneously provided in the medical image analysis apparatus 1000. Here, in the case of the wireless type, a wireless local area network (WLAN)-based communication method such as Wi-Fi may be mainly used. Alternatively, in the case of the wireless type, cellular communication, for example, Long Term Evolution (LTE), or a 5G-based communication method may be used. However, the wireless communication protocol is not limited to the above-described example, and any suitable wireless type communication method may be used. In the case of the wired type, local area network (LAN) and Universal Serial Bus (USB) communication are representative examples, and other methods are also possible.

A memory 1200 of the medical image analysis apparatus 1000 may store various types of information. The various types of data may be temporarily or semi-permanently stored in the memory 1200. Examples of the memory 1200 may include a hard disk drive (HDD), a solid state drive (SSD), a flash memory, a read-only memory (ROM), a random access memory (RAM), and the like. The memory 1200 may be provided in a form in which it is embedded in the medical image analysis apparatus 1000 or in a detachable form. The memory 1200 may store various types of data necessary for the operation of the medical image analysis apparatus 1000 in addition to an operating system (OS) for driving the medical image analysis apparatus 1000 or a program for operating each component of the medical image analysis apparatus 1000.

The controller 1300 may control the overall operation of the medical image analysis apparatus 1000. For example, the controller 1300 may control the overall operation of the medical image analysis apparatus 1000 such as an operation of detecting a region of interest (ROI) or a target joint spacing region from a target medical image, an operation of quantifying a width of a joint part, an operation of quantifying joint spacing, and an operation of calculating joint condition information. Specifically, the controller 1300 may load and execute a program for the overall operation of the medical image analysis apparatus 1000 from the memory 1200. The processor may be implemented as an application processor (AP), a central processing unit (CPU), a microcontroller unit (MCU), or a similar device thereto according to hardware, software, or a combination thereof. In this case, in a hardware manner, the controller may be provided in the form of an electronic circuit for processing an electrical signal to perform a control function, and in a software manner, the controller may be provided in the form of a program or code for driving hardware-type circuits.

Meanwhile, although not illustrated in FIG. 1, the medical image analysis apparatus 1000 may include any suitable input unit and/or output unit. Specifically, the medical image analysis apparatus 1000 may receive a user input necessary for analyzing the medical image through the input unit. For example, the medical image analysis apparatus 1000 may acquire a user input for allocating label information to each of the plurality of regions included in the medical image through the input unit. As another example, the medical image analysis apparatus 1000 may acquire, through the input unit, a user input for setting a section of interest in a joint spacing region for acquiring a joint spacing value.

Also, the medical image analysis apparatus 1000 may output, through an output unit, a result of comparing a target joint condition indicator and/or a target joint condition indicator to be described later with a reference joint condition indicator.

Hereinafter, an operation of the medical image analysis apparatus 1000 according to the embodiment of the present disclosure will be described in detail with reference to FIGS. 2 to 13.

The medical image analysis apparatus 1000 according to the embodiment of the present disclosure may detect the joint spacing region from the medical image. Also, the medical image analysis apparatus 1000 may calculate the joint condition information based on the joint spacing region.

Figure 2:
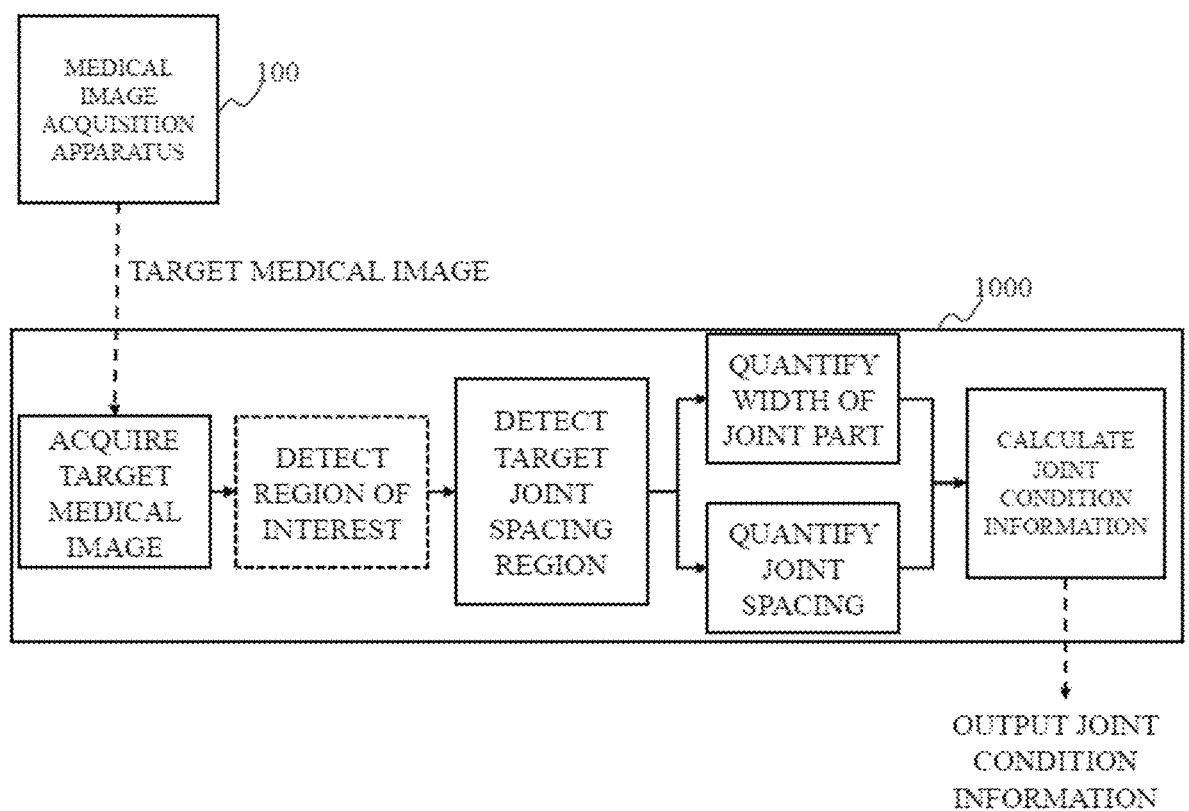
FIG. 2 is a diagram illustrating operations of a medical image analysis apparatus according to an embodiment of the present disclosure.

FIG. 2 is a diagram illustrating operations of the medical image analysis apparatus 1000 according to the embodiment of the present disclosure.

The medical image analysis apparatus 1000 according to the embodiment of the present disclosure may include an image acquisition unit. Specifically, the image acquisition unit of the medical image analysis apparatus 1000 may acquire the target medical image acquired from the medical image acquisition apparatus 100. For example, the image acquisition unit may acquire the target medical image from any external device including the medical image acquisition apparatus 100 through the transceiver 1100.

The medical image analysis apparatus 1000 according to the embodiment of the present disclosure may include a region of interest (ROI) detector.

The ROI detector of the medical image analysis apparatus 1000 according to the embodiment of the present disclosure may detect the ROI included in the target medical image. For example, the ROI detector may detect the ROI including the joint region from the target medical image. Here, the joint region may include the joint spacing region and/or the bone region adjacent to the joint spacing region as described above.

Specifically, the ROI detector may detect the ROI by using an artificial intelligence technique. An operation of detecting the ROI will be described in detail with reference to FIGS. 4 and 5. However, the operation of detecting the ROI from the target medical image may be omitted. For example, when the joint spacing region to be described later can be directly detected from the target medical image, the operation of detecting the ROI by the ROI detector may be omitted.

The medical image analysis apparatus 1000 according to the embodiment of the present disclosure may include a joint spacing region detector. The joint spacing region detector of the medical image analysis apparatus 1000 according to the embodiment of the present disclosure may detect the target joint spacing region from the target medical image. For example, the joint spacing region detector may detect the target joint spacing region from the ROI that includes the joint region included in the target medical image. Here, the target joint spacing region may be any inter-joint region included in the target medical image. According to the embodiment, the joint spacing region detector may acquire the target joint spacing region by using the artificial intelligence technique. For example, the joint spacing region detector may acquire the target joint spacing region using a neural network model trained based on a training set in which the inter-joint region (or joint spacing region) is allocated (or labeled) in the medical image. The content of acquiring the target joint spacing region will be described in detail with reference to FIGS. 4 to 9.

The medical image analysis apparatus 1000 according to the embodiment of the present disclosure may include a joint condition quantification analyzer. In this case, the joint condition quantification analyzer may include a joint width analyzer and a joint spacing analyzer. The joint condition quantification analyzer of the medical image analysis apparatus 1000 according to the embodiment of the present disclosure may calculate the joint condition information based on the joint region and/or the target joint spacing region.

The joint width analyzer of the medical image analysis apparatus 1000 may perform an operation of quantifying the width of the joint part based on the joint region included in the target medical image. For example, the joint width analyzer of the medical image analysis apparatus 1000 may detect an outer point of the joint part by using any image processing technique or artificial intelligence technique, and may calculate quantitative information related to the width of the joint part based on coordinate information of the outer point. The content of quantifying the width of the joint part will be described in detail with reference to FIGS. 10 and 11.

The joint spacing analyzer of the medical image analysis apparatus 1000 according to the embodiment of the present disclosure may perform an operation of quantifying the joint spacing based on the target joint spacing region. For example, the joint spacing analyzer of the medical image analysis apparatus 1000 may acquire a section of interest related to the target joint spacing region and acquire at least one joint spacing value within the section of interest. Also, the joint spacing analyzer of the medical image analysis apparatus 1000 may calculate the quantitative information related to the joint spacing based on at least one joint spacing value. The content of quantifying the joint spacing will be described in detail with reference to FIGS. 12 and 13.

The medical image analysis apparatus 1000 according to the embodiment of the present disclosure may calculate the joint condition information based on the quantitative information related to the width of the joint part and the quantitative information related to the joint spacing. For example, the joint condition quantification analyzer of the medical image analysis apparatus 1000 may calculate a joint condition indicator indicating a joint condition based on the quantitative information related to the width of the joint part and the quantitative information related to the joint spacing.

Figure 3:
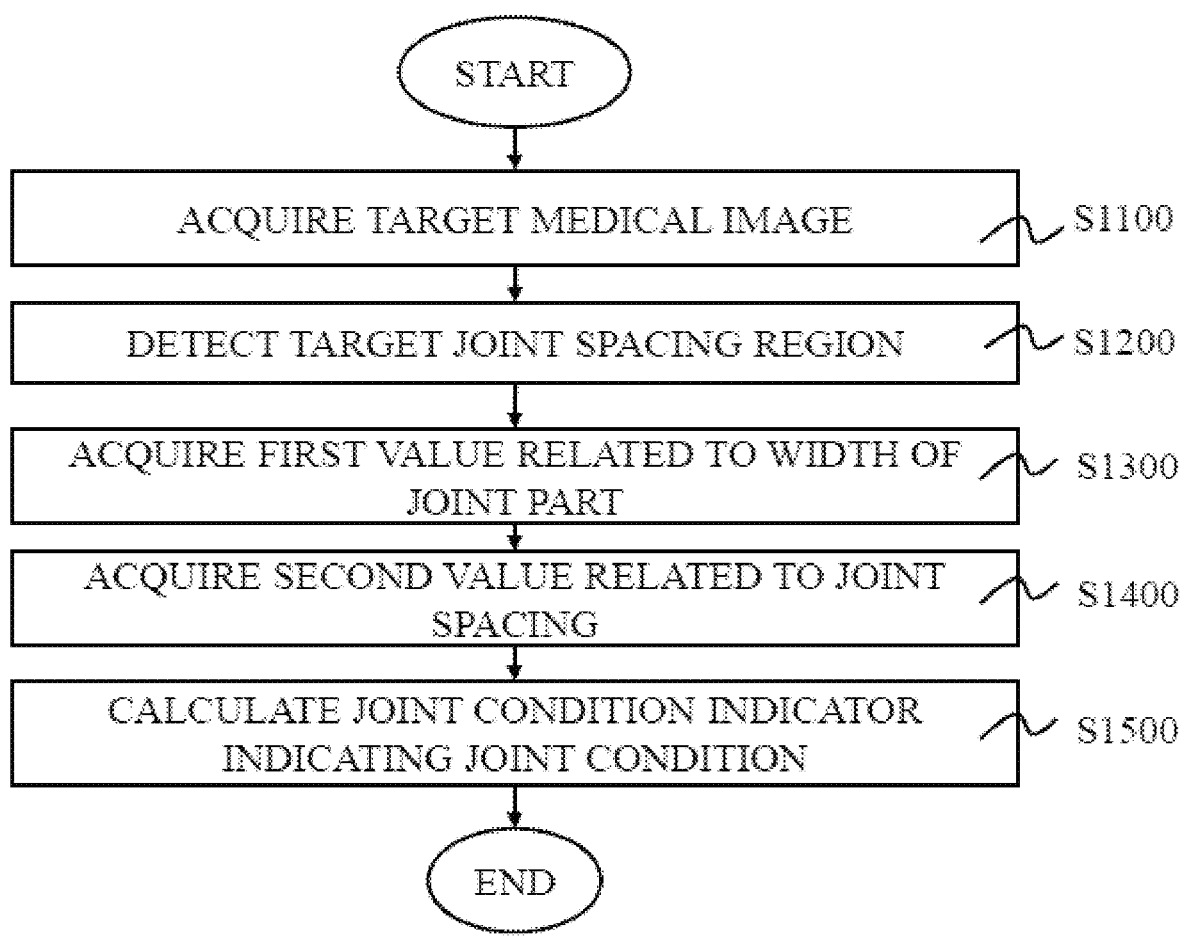
FIG. 3 is a flowchart illustrating a medical image analysis method according to an embodiment of the present disclosure.

FIG. 3 will now be referred to. FIG. 3 is a flowchart of a medical image analysis method according to the embodiment of the present disclosure.

The medical image analysis method according to the embodiment of the present disclosure may include acquiring a target medical image (S1100), detecting a target joint spacing region (S1200), acquiring a first value related to a width of a joint part (S1300), acquiring a second value related to joint spacing (S1400), and calculating a target joint condition indicator indicating the joint condition (S1500).

In the acquiring of the target medical image (S1100), the medical image analysis apparatus 1000 may acquire the target medical image to be analyzed. For example, the medical image analysis apparatus 1000 may acquire the target medical image from the medical image acquisition apparatus 100 or any external device including a database through the transceiver 1100.

In the detecting of the target joint spacing region (S1200), the medical image analysis apparatus 1000 may detect the target joint spacing region from the target medical image. For example, the medical image analysis apparatus 1000 may be implemented to acquire a region including the joint part included in the target medical image as the ROI from the target medical image, and acquire the target joint spacing region by precisely analyzing the ROI. As another example, the medical image analysis apparatus 1000 may be implemented to acquire the target joint spacing region included in the target medical image from the target medical image.

Hereinafter, an embodiment in which the ROI is acquired from the target medical image and the target joint spacing region is acquired by precisely analyzing the ROI will be mainly described, but this is only an example and should not be interpreted as limiting.

Figure 4:
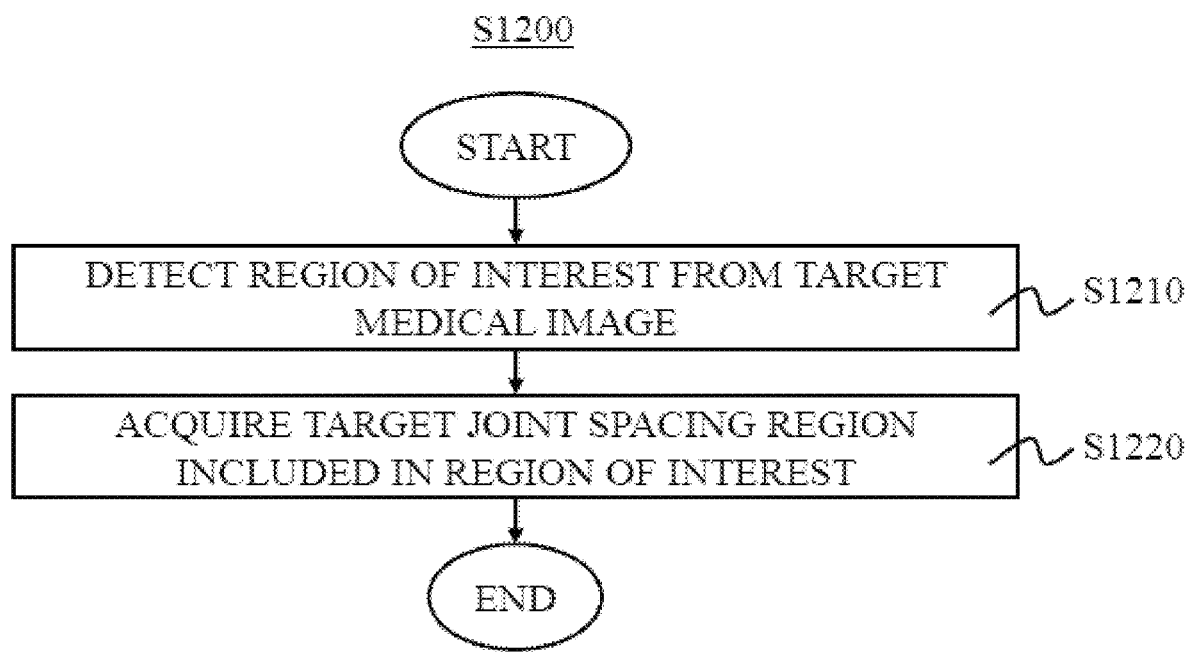
FIG. 4 is a flowchart illustrating an operation of detecting a target joint spacing region in detail according to an embodiment of the present disclosure.
Figure 5:
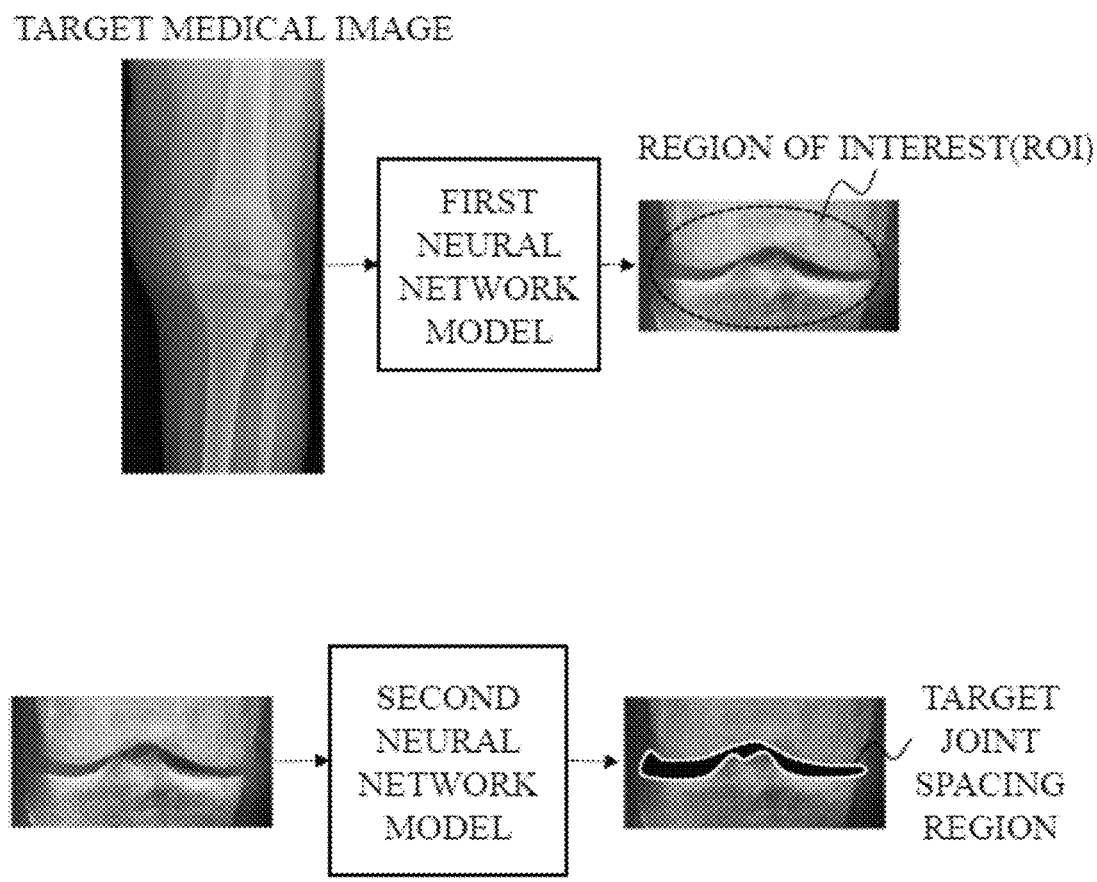
FIG. 5 is a diagram illustrating an aspect of detecting a region of interest (ROI) and a target joint spacing region according to an embodiment of the present disclosure.

FIGS. 4 and 5 will now be referred to. FIG. 4 is a flowchart illustrating an operation of detecting a target joint spacing region in detail according to an embodiment of the present disclosure. FIG. 5 is a diagram illustrating an aspect of detecting the ROI and the target joint spacing region according to an embodiment of the present disclosure.

The acquiring of the target joint spacing region (S1200) may include detecting the ROI from the target medical image (S1210) and acquiring the target joint spacing region included in the ROI (S1220).

In the detecting of the ROI from the target medical image (S1210), the medical image analysis apparatus 1000 may be implemented to detect the region including the joint part from the target medical image as the ROI. For example, the medical image analysis apparatus 1000 may acquire the region including the joint part as the ROI by using any suitable artificial intelligence technique. Specifically, the medical image analysis apparatus 1000 may be implemented to receive the target medical image and detect an ROI using a first neural network model trained to output the region including the joint part as the ROI.

Here, the first neural network model may be trained based on the medical image and the label information allocated to the medical image as the joint part region. In this case, the label information may be automatically allocated to the medical image using any software or may be manually allocated to the medical image by any operator. More specifically, the first neural network model may be trained to receive the medical image and to minimize a difference between an output value and the label information related to the joint part region. Meanwhile, the first neural network model may be a deep learning-based artificial neural network model. Specific examples of the artificial neural network may include a convolutional neural network, a recurrent neural network, a deep neural network, a generative adversarial network, and the like. However, these are merely examples, and the network should be interpreted in a comprehensive sense including all of the above-described artificial neural networks, various other types of artificial neural networks, and artificial neural networks of a combination thereof, and is not necessarily the deep learning-based artificial neural network model.

In the acquiring of the target joint spacing region included in the ROI (S1220), the medical image analysis apparatus 1000 may detect the target joint spacing region from the target medical image. Specifically, the medical image analysis apparatus 1000 may perform segmentation on the ROI of the target medical image to acquire the target joint spacing region including the inter-joint region. For example, the segmentation of the ROI may be performed using any suitable artificial intelligence technique.

Referring back to FIG. 5, the medical image analysis apparatus 1000 may be implemented to detect the target joint spacing region by using a second neural network model trained to receive the target medical image including the ROI and output the inter-joint region.

According to an example, the neural network model may be used as a model for acquiring the target joint spacing region. The neural network model may be provided as a machine learning model. An artificial neural network may be a representative example of the machine learning model. Specifically, a representative example of the artificial neural network is a deep learning-based artificial neural network that includes an input layer that receives data, an output layer that outputs a result, and a hidden layer that processes data between the input and output layers. Specific examples of the artificial neural network include a convolution neural network, a recurrent neural network, a deep neural network, a generative adversarial network, and the like. In the present specification, the neural network should be interpreted in a comprehensive sense including all of the artificial neural networks described above, various other types of artificial neural networks, and artificial neural networks in a combination thereof, and does not necessarily have to be a deep learning series.

In addition, the machine learning model does not necessarily have to be in the form of the artificial neural network model, and in addition, there may be a nearest neighbor algorithm (KNN), random forest, a support vector machine (SVM), principal component analysis (PCA), etc. Alternatively, the above-described techniques may include an ensemble form or a form in which various other methods are combined. On the other hand, it is stated in advance that the artificial neural network can be replaced with another machine learning model unless otherwise specified in the embodiments where the artificial neural network is mainly described.

Furthermore, in the present specification, an algorithm for acquiring the target joint spacing region is not necessarily limited to the machine learning model. That is, the algorithm for acquiring the target joint spacing region may include various judgment/determination algorithms instead of the machine learning model. Therefore, in this specification, it is to be understood that the algorithm for acquiring the target joint spacing region should be understood with a comprehensive meaning including all types of algorithms for calculating the joint spacing region based on the medical image. Hereinafter, however, for convenience of description, the artificial neural network model will be mainly described.

Hereinafter, the content of acquiring the target joint spacing region using the neural network model according to the embodiment of the present disclosure will be described with reference to FIGS. 6 to 9. Specifically, the content of training the neural network model for acquiring the target joint spacing region according to the embodiment of the present disclosure will be described with reference to FIGS. 6 and 7. In addition, the content of acquiring the target joint spacing region using the trained neural network model with reference to FIGS. 8 and 9 will be described.

Figure 6:
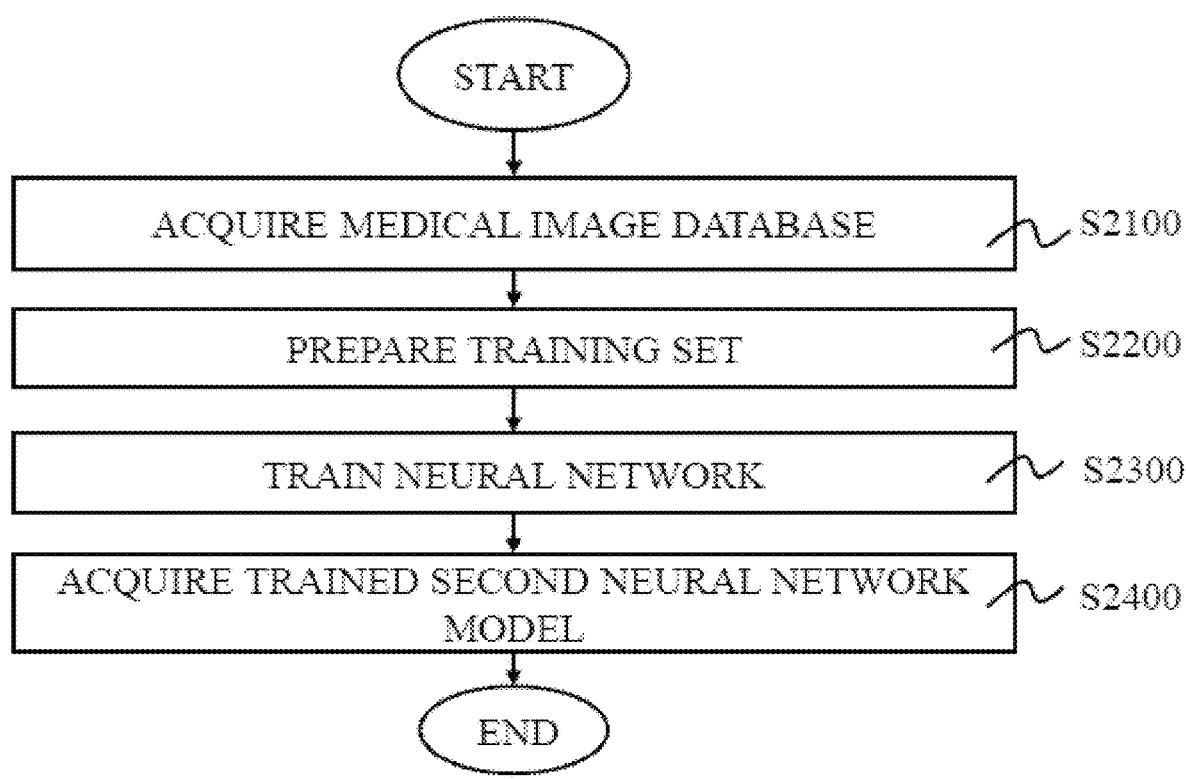
FIG. 6 is a flowchart illustrating a method of training a neural network model for acquiring a target joint spacing region according to an embodiment of the present disclosure.

FIG. 6 will now be referred to. FIG. 6 is a flowchart illustrating a method of training a neural network model for acquiring a target joint spacing region according to an embodiment of the present disclosure. The method of training a neural network model for acquiring a target joint spacing region may be performed in the medical image analysis apparatus 1000. However, the method of learning a neural network model for acquiring a target joint spacing region may also be performed in a separate external device from the medical image analysis apparatus 1000. Hereinafter, it will be described that the training of the neural network model for acquiring the target joint spacing region in the medical image analysis apparatus 1000 is performed. However, this is only an example, and should not be construed as limiting.

The method of training a neural network model for acquiring a target joint spacing region according to the embodiment of the present disclosure may include acquiring a medical image database (S2100), preparing a training set (S2200), training a neural network (S2300), and acquiring the trained neural network model (S2400).

In the acquiring of the medical image database (S2100), the medical image analysis apparatus 1000 may acquire a medical image database including a plurality of medical images from the medical image acquisition apparatus 100 or an external device including an arbitrary database.

In the preparing of the training set (S2200), the medical image analysis apparatus 1000 may acquire the prepared training set by allocating label information to the inter-joint region included in the medical image. The operation of allocating the label information to the inter-joint region may be performed using any suitable software, or may be manually performed by any operator, similar to the above.

In the training of the neural network (S2300), the medical image analysis apparatus 1000 may train the neural network model based on the medical image and the training set.

Figure 7:
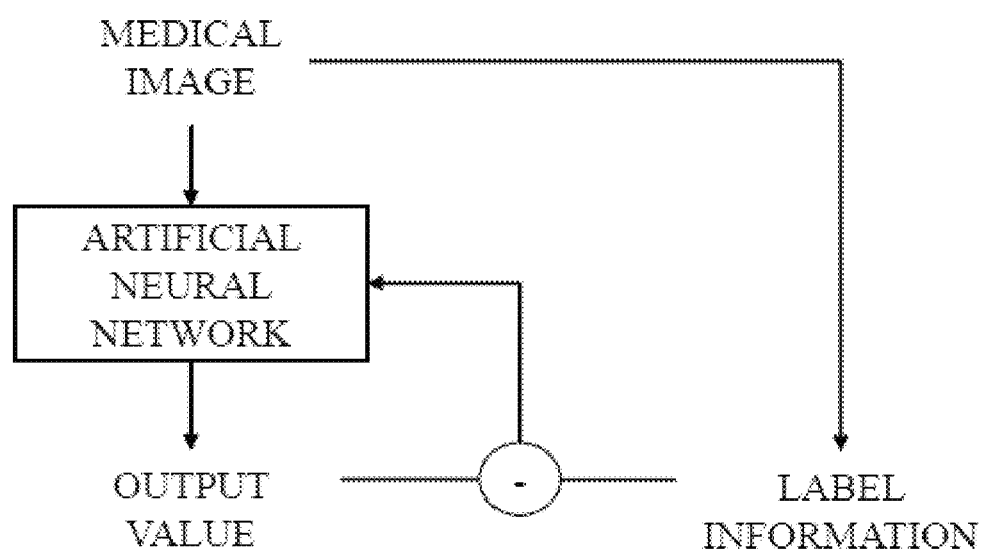
FIG. 7 is a flowchart illustrating an aspect of training a neural network model for acquiring a target joint spacing region according to the embodiment of the present disclosure.

FIG. 7 will now be referred to. FIG. 7 is a flowchart illustrating an aspect of training a neural network model for acquiring a target joint spacing region according to the embodiment of the present disclosure.

The neural network model may include an input layer, an output layer, and a hidden layer. The input layer may receive a medical image, and the output layer may output an output value related to the inter-joint region. The hidden layer may have a plurality of nodes connecting the input layer and the output layer.

The medical image analysis apparatus 1000 according to the embodiment of the present disclosure may train a neural network to output joint spacing region information indicating an inter-joint region based on a medical image. Specifically, the medical image analysis apparatus 1000 may input the medical image to the input layer, and may acquire the output value related to the inter-joint region through the output layer. In addition, the medical image analysis apparatus 1000 may adjust weights (or parameters) of nodes included in the hidden layer based on the difference between the label information and the output value related to the joint spacing region included in the training set. For example, the medical image analysis apparatus 1000 may input a first medical image acquired from the medical image database to the input layer, and update the weights (or parameters) of the nodes included in the hidden layer based on the difference between the output value output through the output layer and the first label information allocated to the joint spacing region of the first medical image. In addition, the medical image analysis apparatus 1000 may input an $N^{th}$ medical image acquired from the medical image database to the input layer, and repeatedly update the weights (or parameters) of the nodes included in the hidden layer based on the difference between the output value output through the output layer and the $N^{th}$ label information allocated to the joint spacing region of the $N^{th}$ medical image.

Specifically, the medical image analysis apparatus 1000 may train the neural network model by repeatedly adjusting the weights (or parameters) of the nodes included in the hidden layer so that the difference between the label information and the output value related to the joint spacing region is minimized.

Referring back to FIG. 6, the method of training a neural network model for acquiring a target joint spacing region according to the embodiment of the present disclosure may include acquiring a trained second neural network model (S2400). In the acquiring of the trained second neural network model (S2400), the medical image analysis apparatus 1000 may acquire the output value output through the output layer and the weights or parameters of the nodes included in the hidden layer trained so that the output value and label information output through the output layer are minimized. Alternatively, in the acquiring of the trained second neural network model (S1400), the medical image analysis apparatus 1000 may acquire the second neural network model that includes the hidden layer including the nodes having the above-described weights or parameters.

Meanwhile, although not illustrated in FIG. 6, the neural network model for acquiring the target joint spacing region according to the embodiment of the present disclosure may further include verifying the neural network. For example, the medical image analysis apparatus 1000 may verify the neural network model based on at least a part of the training set. Specifically, the medical image analysis apparatus 1000 may input at least some of the medical images included in the training set to the input layer of the neural network model, and acquire the output value output through the output layer. In addition, the medical image analysis apparatus 1000 may compare similarity between the output value and the label information related to the medical image included in the training set to verify whether the weights (or parameters) of the node included in the hidden layer of the neural network model are appropriate.

Meanwhile, the target medical image may include a plurality of joint regions. For example, a bone image may include several joint regions. In this case, the medical image analysis apparatus 1000 according to the embodiment of the present disclosure may be implemented to train the neural network model for each joint region and detect the joint spacing region using at least one neural network model trained for each joint region. For example, the medical image analysis apparatus 1000 may be configured so that, for the first joint region, the joint spacing region included in the first joint region is detected using the trained first joint detection neural network model, and for the second joint region, the joint spacing region included in the second joint region is detected using the trained second joint detection neural network model. However, this is only an example, and a single neural network model may be used in a case where a shape of the inter-joint region is similar.

Figure 8:
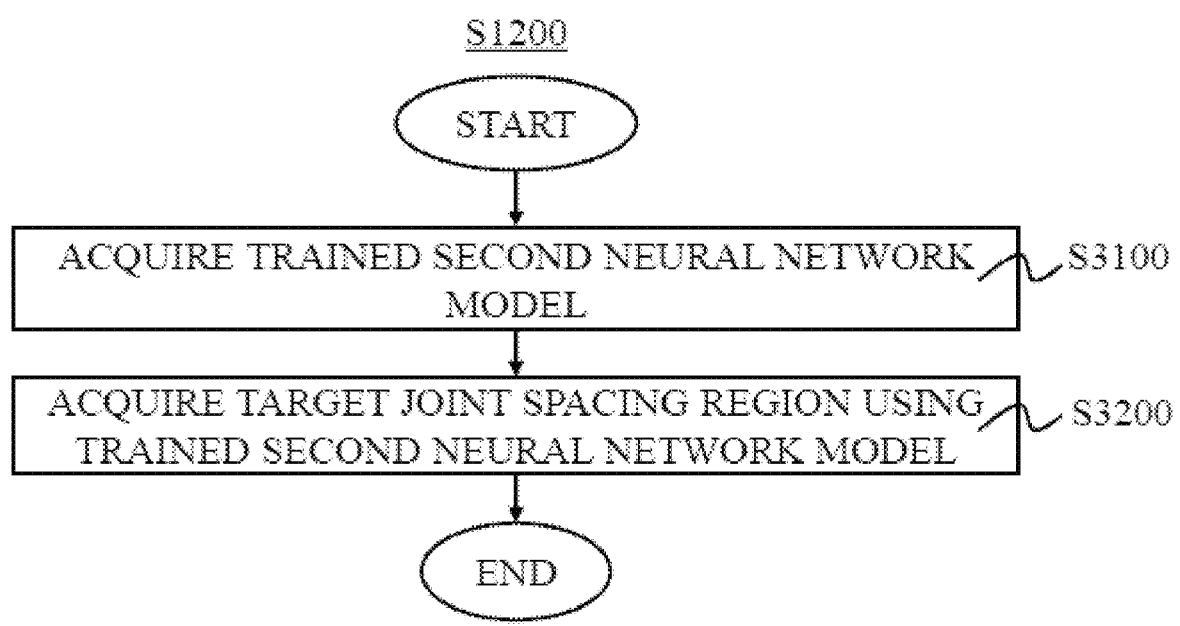
FIG. 8 is a flowchart illustrating the operation of detecting the target joint spacing region in detail according to the embodiment of the present disclosure.

FIG. 8 will now be referred to. FIG. 8 is a flowchart illustrating the operation of detecting the target joint spacing region in detail according to the embodiment of the present disclosure.

The detecting of the target joint spacing region according to the embodiment of the present disclosure (S1200) may include acquiring the trained second neural network model (S3100) and acquiring the target joint spacing region using the trained second neural network model (S3200).

In the acquiring of the trained second neural network model (S3100), the medical image analysis apparatus 1000 may acquire the trained second neural network model. For example, the weights or parameters of the nodes of the second neural network model may be acquired. As another example, the medical image analysis apparatus 1000 may acquire the neural network that includes the hidden layer including the nodes having the weights or parameters acquired through the training.

In the acquiring of the target joint spacing region using the trained second neural network model (S3200), the medical image analysis apparatus 1000 according to the embodiment of the present disclosure may acquire the target joint spacing region based on the trained second neural network model and the target medical image.

Figure 9:
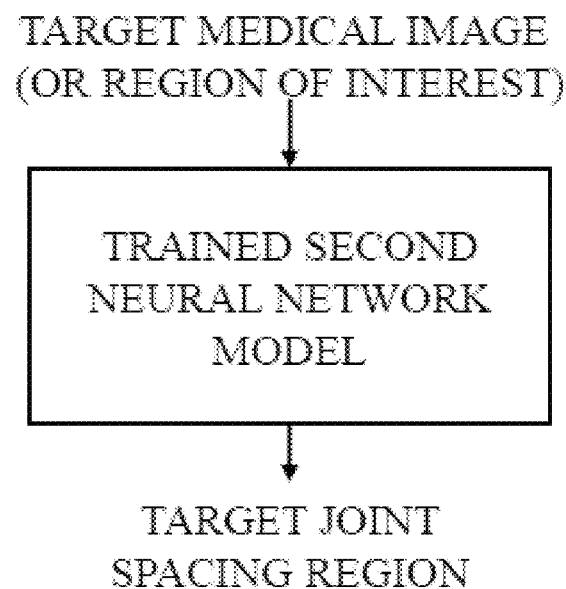
FIG. 9 is a schematic diagram illustrating an aspect of acquiring the target joint spacing region using the trained neural network model according to the embodiment of the present disclosure.

FIG. 9 will now be referred to. FIG. 9 is a schematic diagram illustrating an aspect of obtaining the target joint spacing region using the trained neural network model according to the embodiment of the present disclosure.

The medical image analysis apparatus 1000 may input the target medical image (or a target medical image including an ROI) to the input layer of the trained second neural network model, and acquire the information related to the target joint spacing region through the output layer. Since the trained second neural network model is trained to output the joint spacing region information based on the medical image, the medical image analysis apparatus 1000 may acquire the target joint spacing region included in the target medical image (or a medical image including an ROI) based on the trained second neural network model and the target medical image.

Referring back to FIG. 3, the medical image analysis method according to the embodiment of the present disclosure may include acquiring the first value related to the width of the joint part (S1300).

Figure 10:
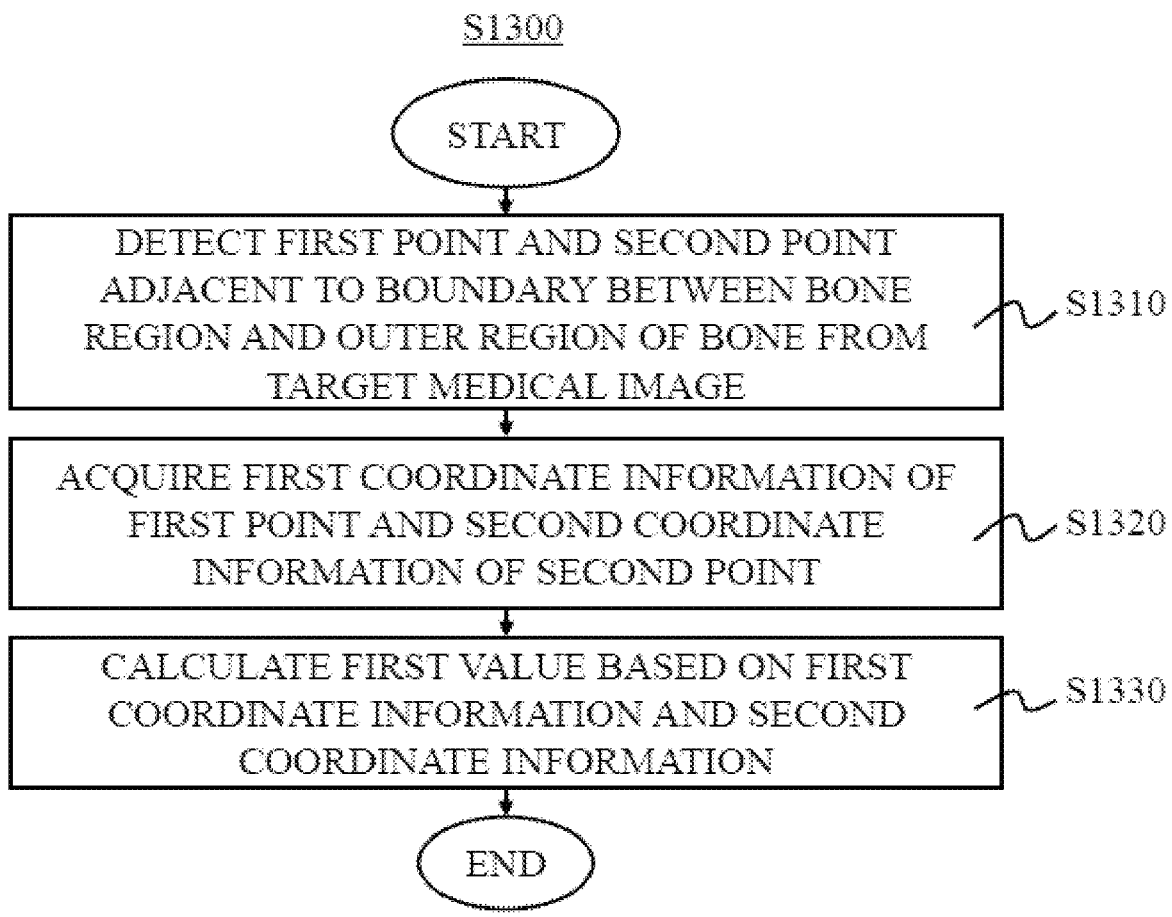
FIG. 10 is a flowchart illustrating an operation of acquiring a first value related to a width of a joint part in detail according to an embodiment of the present disclosure.
Figure 11:
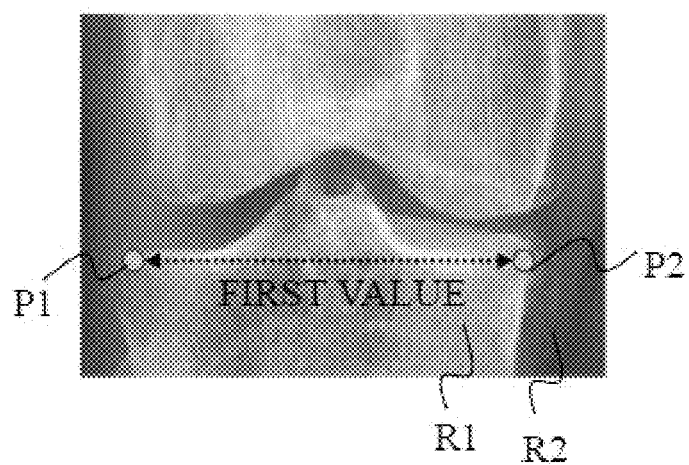
FIG. 11 is a diagram illustrating an aspect of acquiring the first value according to the embodiment of the present disclosure.

FIGS. 10 and 11 will now be referred to. FIG. 10 is a flow chart illustrating the operation (S1300) of obtaining the first value related to the width of the joint part in detail according to the embodiment of the present disclosure. FIG. 11 is a diagram illustrating an aspect of obtaining the first value according to the embodiment of the present disclosure.

According to the embodiment of the present disclosure, the acquiring of the first value (S1300) may include detecting a first point and a second point adjacent to a boundary between a bone region and an outer region of a bone from the target medical image (S1310), acquiring first coordinate information of the first point and second coordinate information of the second point (S1320); and calculating the first value based on the first coordinate information and the second coordinate information (S1330).

In the detecting of the first point and the second point adjacent to the boundary between the bone region and the outer region of the bone from the target joint spacing region (S1310), the medical image analysis apparatus 1000 may detect the inter-joint region, the adjacent bone region, and the outer region of the bone included in the target medical image. In detail, the medical image analysis apparatus 1000 may detect a first point P1 and a second point P2 adjacent to a boundary between a bone region R1 adjacent to a joint and an outer region R2 of a bone from the target medical image (or the medical image including the ROI).

For example, the medical image analysis apparatus 1000 may detect the first point P1 and the second point P2 using an arbitrary image processing technique. For example, the medical image analysis apparatus 1000 may process the target medical image by using the arbitrary image processing technique, and detect the first point P1 and the second point P2 based on the brightness of the processed target medical image. Specifically, the medical image analysis apparatus 1000 may acquire the boundary between the bone region R1 and the outer region R2 of the bone based on a difference between first brightness of the bone region R1 and second brightness of the outer region R2 of the bone, and acquire the first point P1 and the second point P2 adjacent to the boundary.

As another example, the medical image analysis apparatus 1000 may detect the first point P1 and the second point P2 using an arbitrary image processing technique. For example, the medical image analysis apparatus 1000 may train a neural network model for acquiring both end points of a bone based on the medical image and label information on both end points of the bone adjacent to the inter-joint region. In this case, the medical image analysis apparatus 1000 may detect both end points of the bone, for example, the first point P1 and the second point P2, using the trained neural network model.

In the acquiring of the first coordinate information of the first point and the second coordinate information of the second point (S1320), the medical image analysis apparatus 1000 may acquire the coordinate information of the detected first point P1 and second point P2. Specifically, the target medical image may include a plurality of cells (for example, pixels or voxels), and the target medical image may include the coordinate information of the cells. In this case, the medical image analysis apparatus 1000 may acquire the first coordinate information based on the coordinates of the cell corresponding to the first point P1, and acquire the second coordinate information based on the coordinates of the cell corresponding to the second point P2.

In the calculating of the first value based on the first coordinate information and the second coordinate information (S1330), the medical image analysis apparatus 1000 may acquire the first value related to the width of the joint part based on the first coordinate information and the second coordinate information. For example, as illustrated in FIG. 11, in the target medical image in which two bones are positioned vertically, when the first coordinate information (for example, $e1(x,y)$) of the first point P1 and the second coordinate information (for example, $e2(x,y)$) of the second point P2 that are both end points of the bone are acquired, the medical image analysis apparatus 1000 may be implemented to calculate the first value related to the width of the joint part as $|e1(x,y)-e2(x,y)|$ using a method of calculating a Euclidean distance. However, this is only an example of description, and the medical image analysis apparatus 1000 may be implemented to calculate the first value related to the width of the joint part in consideration of the alignment direction of the target medical image.

Referring back to FIG. 3, the medical image analysis method according to the embodiment of the present disclosure may include acquiring the first value related to the joint spacing (S1400).

Figure 12:
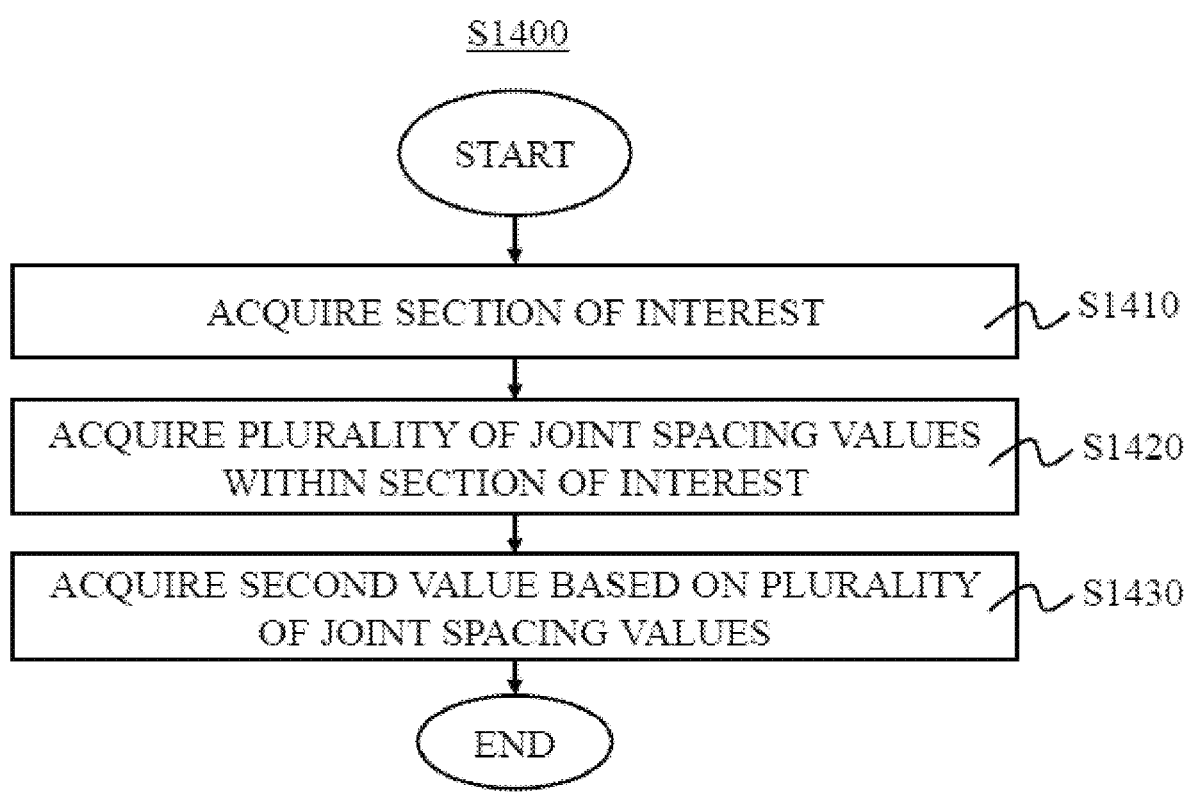
FIG. 12 is a flowchart illustrating an operation of acquiring a second value related to the joint spacing in detail according to the embodiment of the present disclosure.
Figure 13:
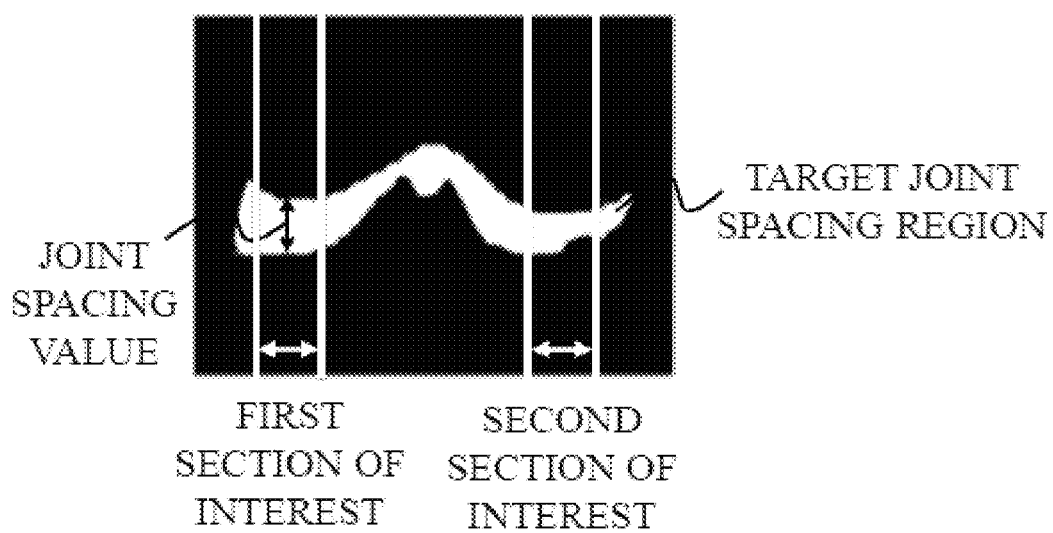
FIG. 13 is a diagram illustrating an aspect of acquiring the second value according to the embodiment of the present disclosure.

FIGS. 12 and 13 will now be referred to. FIG. 12 is a flowchart illustrating an operation of acquiring the second value related to the joint spacing in detail according to the embodiment of the present disclosure (S1400). FIG. 13 is a diagram illustrating an aspect of acquiring the second value according to the embodiment of the present disclosure.

According to the embodiment of the present disclosure, the acquiring of the second value (S1400) may include acquiring a section of interest in the joint spacing region (S1410), acquiring a plurality of joint spacing values within the section of interest (S1420), and acquiring the second value based on the plurality of joint spacing values (S1430).

In the acquiring of the section of interest from the joint space region (S1410), the medical image analysis apparatus 1000 may acquire the section of interest. As an example, the medical image analysis apparatus 1000 may acquire the inter-joint region known to have high clinical importance in identifying the joint condition as a section of interest. For example, in the case of a knee joint, a section that has cartilage and is known as a region related to severe pain due to arthritis may be acquired as a section of interest.

For example, the section of interest may be automatically acquired using both end points (for example, the first point P1 and the second point P2) of the bone described above, the width (for example, the first value) between both end points of the bone, the statistical ratio of the clinically important section described above, or the like. As another example, a user may input the section of interest through any input unit, and the medical image analysis apparatus 1000 may acquire the section of interest based on the user input.

On the other hand, the section of interest may be divided into several subsections and may be continuous or discontinuous.

In the acquiring of the plurality of joint spacing values within the section of interest (S1420), the medical image analysis apparatus 1000 may acquire at least one joint spacing value within the section of interest. For example, the medical image analysis apparatus 1000 may acquire at least one joint spacing value of the inter-joint region within the first section of interest. In addition, the medical image analysis apparatus 1000 may acquire at least one joint spacing value of the joint spacing region within the second section of interest.

The coordinate information of the joint spacing region may be used for the medical image analysis apparatus 1000 to acquire the joint spacing value. For example, the medical image analysis apparatus 1000 may be implemented to acquire the joint spacing value based on the coordinate information of the boundary defining the joint spacing region within the section of interest (for example, a first section of interest or a second section of interest). However, this is only an example, and the medical image analysis apparatus 1000 may acquire the joint spacing value within the section of interest using any suitable method.

In the acquiring of the second value based on the plurality of joint spacing values (S1430), the medical image analysis apparatus 1000 may acquire the second value related to the joint spacing based on at least one joint spacing value acquired from the target joint spacing region within the section of interest. For example, the medical image analysis apparatus 1000 may acquire a minimum value among the plurality of joint spacing values as the second value related to the joint spacing. As another example, the medical image analysis apparatus 1000 may acquire an average value of the plurality of joint spacing values as the second value related to the joint spacing. As another example, the medical image analysis apparatus 1000 may acquire the second value by assigning any appropriate weight to the minimum value among the plurality of joint spacing values and the average value of the plurality of joint spacing values.

Referring back to FIG. 3, the medical image analysis method may include calculating a target joint condition indicator indicating a joint condition according to an embodiment of the present disclosure (S1500).

In the calculating of the target joint condition indicator indicating the joint condition (S1500), the medical image analysis apparatus 1000 may calculate the target joint condition indicator based on the first value related to the width of the joint part and the second value related to the joint spacing. For example, the medical image analysis apparatus 1000 may calculate the target joint condition indicator defined as a ratio of the second value to the first value. Specifically, when the second value is the minimum joint spacing value, the medical image analysis apparatus 1000 may calculate the minimum joint spacing value compared to the first value (the width value of the joint part) as the target joint condition indicator. Alternatively, when the second value is the average spacing value, the medical image analysis apparatus 1000 may calculate the average joint spacing value compared to the first value (the width value of the joint part) as the target joint condition indicator.

The target joint condition indicator acquired according to the embodiment of the present disclosure may be quantified by linking the joint spacing value that is affected by various external factors such as race, sex, and age with the width of the joint part. Accordingly, the target joint condition indicator acquired according to the embodiment of the present disclosure may minimize the influence of various external factors such as race, sex, and age, and provide objective joint condition information.

On the other hand, the medical image analysis apparatus 1000 according to the embodiment of the present disclosure may perform an operation of comparing and analyzing a target joint condition indicator with a reference joint condition indicator of a normal joint group. Specifically, the medical image analysis apparatus 1000 may acquire a joint condition data set from an arbitrary database. In this case, the joint condition data set may include a reference medical image representing a normal joint, a width value of a joint part calculated from the reference medical image, a joint spacing value calculated from the reference medical image, and the like.

The medical image analysis apparatus 1000 may calculate a reference joint condition indicator of a normal group from the joint condition data set. For example, the medical image analysis apparatus 1000 may calculate the first joint condition indicator (for example, a minimum joint spacing value compared to a width value of a joint part) from a first reference medical image related to the normal joint, and the second condition indicator (for example, the minimum joint spacing value compared to the width value of the joint part) from the medical image related to the normal joint. In addition, the medical image analysis apparatus 1000 may calculate the reference joint condition indicator based on the first joint condition indicator and the second joint condition indicator. For example, the reference joint condition indicator may be calculated as the average value of the plurality of joint condition indicators of the normal group, including the first joint condition indicator and the second joint condition indicator.

The medical image analysis apparatus 1000 according to the embodiment of the present disclosure may quantify the target joint condition indicator by comparing the target joint condition indicator with the reference joint condition indicator. As an example, the medical image analysis apparatus 1000 may calculate a reduction rate of the target joint condition indicator compared to the reference joint condition indicator. As an example, the reduction rate may be defined as ((reference joint condition indicator−target joint condition indicator)/reference joint condition indicator)*100. For example, when a reference joint condition indicator (for example, a minimum joint spacing value compared to the width value of the joint part), which is an average value of joint condition indicators of normal groups, is 0.22, and the target joint condition indicator (for example, the minimum joint spacing value compared to the value of the joint width part) is 0.055, the reduction rate may be calculated as about 75%. In other words, the medical image analysis apparatus 1000 may quantify the reduction rate indicating a state in which a joint condition of a subject to be analyzed has a reduction rate of 75% compared to the normal joint, and thus the joint spacing is narrowed compared to the normal joint.

As another example, when a reference joint condition indicator (for example, the minimum joint spacing value compared to the width value of the joint part), which is an average value of joint condition indicators of knees of normal groups, is 0.06, and the target joint condition indicator (for example, the minimum joint spacing value compared to the value of the joint width part) is 0.015, the reduction rate may be calculated as about 75%. In other words, the medical image analysis apparatus 1000 may quantify the reduction rate indicating a state in which the joint condition of the subject to be analyzed has a reduction rate of 75% compared to a normal knee, and thus the knee joint spacing of the subject to be analyzed is narrowed compared to the normal knee joint. However, the above-described numerical values are merely examples for convenience of description, and should not be construed as limiting. Through this comparison analysis, the medical image analysis apparatus 1000 according to the embodiment of the present disclosure may compare states between joints of the same person or analyze the change in the joint conditions over time. In addition, the medical image analysis apparatus 1000 may provide information on a joint condition of a subject to be analyzed by quantifying joint conditions between other persons.

Meanwhile, although not illustrated, the medical image analysis apparatus 1000 according to the embodiment of the present disclosure may output joint condition information or a comparison analysis result with a normal group through any output unit. Alternatively, the medical image analysis apparatus 1000 according to the embodiment of the present disclosure may transmit the acquired target joint condition indicator or the comparison analysis result with the normal group to any external device including the medical image acquisition apparatus 100. Any external device that has received the target joint condition indicator or the comparison analysis result with the normal group may output the joint condition information or the comparison analysis result with the normal group through any output unit.

According to the medical image analysis method, apparatus, and system according to the embodiment of the present disclosure, it is possible to obtain the objective joint condition information by minimizing the influence of external factors such as a body type, race, and sex. In addition, according to the medical image analysis method, apparatus and system according to the embodiment of the present disclosure, it is possible to more accurately estimate the joint condition based on the objective joint condition information.

Various operations of the medical image analysis apparatus 1000 described above may be stored in the memory 1200 of the medical image analysis apparatus 1000, and the controller 1300 of the medical image analysis apparatus 1000 may be provided to perform the operations stored in the memory 1200.

Features, structures, effects, etc., described in the above embodiments are included in at least one embodiment of the present disclosure and are not necessarily limited only to one embodiment. Furthermore, features, structures, effects, etc., illustrated in each embodiment can be practiced by being combined or modified for other embodiments by those of ordinary skill in the art to which the embodiments pertain. Accordingly, the content related to such combinations and modifications should be interpreted as being included in the scope of the present disclosure.

In addition, although the embodiments have been mainly described hereinabove, these are only examples and do not limit the present disclosure. Those skilled in the art to which the present disclosure pertains may understand that several modifications and applications that are not described in the present specification may be made without departing from the spirit of the present disclosure. That is, each component specifically shown in the embodiment may be implemented with modifications. In addition, differences associated with these modifications and applications are to be interpreted as being included in the scope of the present disclosure as defined by the following claims.

The invention claimed is:

1. A medical image analysis method which is performed by an apparatus for acquiring a medical image and performing a morphological analysis of a joint based on the medical image, the medical image analysis method comprising:
   acquiring a target medical image;
   detecting a target joint spacing region from the target medical image;
   acquiring a first value of a width of a joint part from the target medical image;
   acquiring a second value related to joint spacing from the target joint spacing region; and
   calculating a target joint condition indicator indicating a joint condition based on the first value and the second value,
   wherein the target joint condition indicator is defined as a ratio of the second value to the first value.

2. The medical image analysis method of claim 1, wherein the detecting of the target joint spacing region includes:
   detecting a region of interest from the target medical image; and
   performing segmentation on the region of interest to acquire the target joint spacing region included in the region of interest.

3. The medical image analysis method of claim 2, wherein the region of interest is acquired using a first neural network model trained to receive the medical image and output a region including a joint part.

4. The medical image analysis method of claim 3, wherein the segmentation is performed using a second neural network model trained to receive a medical image including a region of interest and output a joint spacing region.

5. The medical image analysis method of claim 1, wherein the acquiring of the first value includes:
   detecting a first point and a second point adjacent to a boundary between a bone region and an outer region of a bone from the target medical image;
   acquiring first coordinate information of the first point and second coordinate information of the second point; and
   calculating the first value based on the first coordinate information and the second coordinate information.

6. The medical image analysis method of claim 5, wherein the first point and the second point are acquired based on a difference between brightness of the bone region included in the target medical image and brightness of the outer region of the bone.

7. The medical image analysis method of claim 5, wherein the first point and the second point are acquired through a neural network model trained to receive a medical image including the bone region and the outer region of the bone and output a first region corresponding to the first point and a second region corresponding to the second point.

8. The medical image analysis method of claim 1, wherein the acquiring of the second value includes:
   acquiring a section of interest in the joint spacing region;
   acquiring a plurality of joint spacing values within the section of interest; and acquiring the second value based on the plurality of joint spacing values.

9. The medical image analysis method of claim 8, wherein the second value is a minimum value among the plurality of joint spacing values or an average value of the plurality of joint spacing values.

10. A non-transitory computer-readable recording medium in which a computer program executed by a computer is recorded, the computer program comprising:
   acquiring a target medical image;
   detecting a target joint spacing region from the target medical image;
   acquiring a first value of a width of a joint part from the target medical image;
   acquiring a second value related to joint spacing from the target joint spacing region; and
   calculating a target joint condition indicator indicating a joint condition based on the first value and the second value,
   wherein the target joint condition indicator is defined as a ratio of the second value to the first value.

11. A medical image analysis apparatus for calculating information related to a joint condition by analyzing a medical image, the medical image analysis apparatus comprising:
   an image acquisition unit configured to acquire a target medical image; and
   a controller configured to provide joint condition information based on the target medical image,
   wherein the controller acquires the target medical image, detects a target joint spacing region from the target medical image, acquires a first value of a width of a joint part from the target medical image, acquires a second value related to joint spacing from the target joint spacing region, and calculates a target joint condition indicator indicating the joint condition based on the first value and the second value,
   wherein the target joint condition indicator is defined as a ratio of the second value to the first value.

* * * * *